United States Patent
Utsunomiya et al.

(10) Patent No.: US 8,155,889 B2
(45) Date of Patent: Apr. 10, 2012

(54) METHOD FOR ASSESSING DEGREE OF RELIABILITY OF NUCLEIC ACID BASE SEQUENCE

(75) Inventors: Shinichi Utsunomiya, Kyoto (JP); Makoto Hazama, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 261 days.

(21) Appl. No.: 12/517,552

(22) PCT Filed: Dec. 4, 2006

(86) PCT No.: PCT/JP2006/324158
§ 371 (c)(1),
(2), (4) Date: Jun. 3, 2009

(87) PCT Pub. No.: WO2008/068831
PCT Pub. Date: Jun. 12, 2008

(65) Prior Publication Data
US 2010/0070189 A1 Mar. 18, 2010

(51) Int. Cl.
*G01N 33/50* (2006.01)
(52) U.S. Cl. ........................................... 702/20
(58) Field of Classification Search .................. 702/20
See application file for complete search history.

(56) References Cited

U.S. PATENT DOCUMENTS

2002/0090630 A1   7/2002   Hazama

FOREIGN PATENT DOCUMENTS

| JP | 2002-168868 A | 6/2002 |
| JP | 2002-228633 A | 8/2002 |
| JP | 2006-300799 A | 11/2006 |

OTHER PUBLICATIONS

International Search Report for the Application No. PCT/JP2006/324158 mailed Mar. 6, 2007.
Ewing, Brent et al., "Base-Calling of Automated Sequencer Traces Using Phred. II. Error Probabilities"; Genome Research, 1998, vol. 8, pp. 186-194.
S. Minami, "Waveform Data Processing for Scientific Measurement", CQ Publishing, 1986, pp. 111-113 and 186-191.

*Primary Examiner* — Jerry Lin
(74) *Attorney, Agent, or Firm* — Cheng Law Group, PLLC (57) ABSTRACT

Disclosed herein is a method for assessing the degree of reliability of a nucleic acid base sequence, by which a higher-accuracy assessment result of the degree of reliability can be obtained as compared to a case where the degree of reliability is assessed based on only the evaluation of analytical data. The method includes the steps: (A) when measured data is processed into analytical data, computing a processing evaluation value $E1_i$ for evaluating quality of measured data of an i-th base and contents of processing having been performed on the measured data of the i-th base; (B) computing an analytical data evaluation value $E2_i$ of the i-th base based on the processed analytical data; and (C) computing a degree of reliability by a predetermined calculation formula using the processing evaluation value $E1_i$ and the analytical data evaluation value $E2_i$.

12 Claims, 4 Drawing Sheets

METHOD FOR ASSESSING DEGREE OF RELIABILITY OF NUCLEIC ACID BASE SEQUENCE

TECHNICAL FIELD

The nucleic acid base sequence of DNA (deoxyribonucleic acid) or the like is determined by assembling (i.e., linking together) nucleic acid base sequence fragments obtained by analyzing measured data obtained from a genetic analyzer using electrophoresis or the like. The present invention relates to a method for assessing the degree of reliability of a nucleic acid base sequence needed for such a sequence assembly process.

BACKGROUND ART

When a genetic analyzer is used to determine the base sequence of DNA, four time-series measured data sets corresponding to four kinds of bases, A (adenine), G (guanine), C (cytosine), and T (thymine) are obtained. According to a conventional method such as Phred (see Non-Patent Document 1), such measured data sets are subjected to processing such as noise elimination and mobility correction for correcting a time lag among time-series data sets resulting from a difference in migration speed among different labeling dyes depending on the kind of base to obtain "analytical data". Then, a nucleic acid base sequence is determined based on the "analytical data", and the degree of reliability of the nucleic acid base sequence is determined by analyzing the characteristic indicators of the "analytical data".

Such a conventional method such as Phred uses, as the characteristic indicators of "analytical data", variations in peak-to-peak intervals, the ratio of the amplitude of a peak having been identified as a nucleic acid base peak to a noise peak, and the distance to a part having an unresolved base. The reliability degree value of each base is assessed by evaluating the measured values of these characteristic indicators in combination. This is based on the findings that highly-reliable "analytical data" is characterized in that peaks are spaced at regular intervals, the ratio of the amplitude of a peak having been identified as a nucleic acid base peak to a noise peak is high, and a part having an unresolved base is not near a peak having been identified as a nucleic acid base peak.

The reliability degree value of each base is referred to as a quality value (hereinafter, sometimes abbreviated as "QV"), and is defined by the following formula (1):

$$QV = -10 \times \mathrm{Log}_{10}(\mathrm{Err})$$

where Err is an error probability (1)

Further, in the case of the conventional method such as Phred, in order to comprehensively evaluate two or more characteristic indicators, statistical data is previously prepared by mapping actual error rates onto parametric space defined by the characteristic indicators. The actual error rates are obtained in such a manner that the base sequences of many samples having known base sequences are determined by measurement and checked against the correct base sequences of these samples. The degree of reliability of a base sequence determined by analyzing measured data is assessed using the formula (1) by reference to the statistical data.

More specifically, an error probability Err (i, j, k) is measured by statistically processing many bases having parameters (Ai, Bj, Ck). In a case where an identified base of an unknown sample has parameters (Ai, Bj, Ck), QV of the base is determined by the formula (1).

Non-Patent Document 1: Ewing B, Green P, Base-calling of automated sequencer traces using phred. II. Error probabilities. Genome Research 8, pp. 186-194, 1998

Non-Patent Document 2: S. Minami, "Waveform data processing for scientific measurement", CQ publishing, pp. 111-113 and pp. 186-191, 1986

Patent Document 1: Japanese Patent Application Laid-open No. 2002-168868

Patent Document 2: Japanese Patent Application Laid-open No. 2002-228633

DISCLOSURE OF THE INVENTION

Problem to be Solved by the Invention

As described above, the conventional method such as Phred uses characteristic indicators measured using "analytical data" obtained by subjecting measured data to processing such as noise elimination and mobility correction for correcting a time lag among time-series data sets resulting from a difference in migration speed among different labeling dyes depending on the kind of base, but cannot use information related to data reliability such as the quality of the measured data and the contents of processing having been performed on the measured data. For example, even in a case where analytical data has a high signal-to-noise ratio, there is no way of knowing whether it results from measured data or from noise-reduction processing. Further, the reliability of processing for performing mobility correction varies depending on whether there was a possibility that mobility correction to allow base peaks to be spaced at regular intervals could be achieved by another correction amount or there was little possibility that mobility correction could be achieved by another correction amount. However, even in a case where base peaks are spaced at regular intervals in analytical data, it is impossible to know which was the case from the analytical data obtained as a result of processing measured data.

Further, as described above, the above-described method uses statistical data showing the correlation between combined characteristic indicators and the degree of reliability, which is previously prepared by measuring the characteristic indicators and calculating error rates by checking the base sequences of many samples having known base sequences determined by analyzing measured date against the correct base sequences of these samples. However, such a correlation does not always apply to unknown samples. For example, in a case where a population forming the statistical data contains a data group showing a special correlation, an error probability is affected by such a data group, and as a result, the reliability degree value outputted based on the error probability also becomes inadequate. Further, in order to obtain statistical data on actual error rates, it is necessary to collect data from many known samples, but it is difficult to collect data sufficient in both quality and quantity as a population.

It is an object of the present invention to obtain a higher-accuracy assessment result of the degree of reliability as compared to a case where the degree of reliability is assessed based on only the evaluation of analytical data.

Means for Solving the Problem

The present invention is directed to a method for assessing the degree of reliability of a nucleic acid base sequence, including the steps of:

(A) computing a processing evaluation value $E1_i$ for evaluating quality of measured data of an i-th base and contents of processing having been performed on the measured data of the i-th base when the measured data is processed into analytical data;

(B) computing an analytical data evaluation value $E2_i$ of the i-th base based on the processed analytical data; and (C) computing a degree of reliability by a predetermined calculation formula, using the processing evaluation value $E1_i$ and the analytical data evaluation value $E2_i$.

The step (C) may be the step of computing a degree of reliability $QV_i$ of an i-th base peak by the following calculation formula:

$$QV_i = -\text{const}QV \times \text{Log}_{10}(\text{Err}_i)$$

where constQV is a correction constant, and $\text{Err}_i$ is an error probability of an i-th base and is represented by the following formula:

$$\text{Err}_i = (1-E1_i) \times (1-E2_i)$$

where $E1_i$ and $E2_i$ are evaluation values, each taking a value between 0 and 1, and have Emax which is a maximum value less than 1. Examples of $E1_i$ and $E2_i$ include, but are not limited to, the following ones.

The step (A) may be the step of computing, as the processing evaluation value $E1_i$ of an i-th base, an evaluation indicator $E11_i$ defined by tire following formula:

$$E1_i = E11_i$$

where $E11_i$ is an evaluation indicator for evaluating a signal-to-noise ratio of measured data of an i-th base peak, and is represented by the following formula:

$$E11_i = E11\max \times (\text{Signal}(i)/\text{Noise}(i))/\text{const}E11$$

where constE11 is a normalized, constant and when (Signal(i)/Noise(i))$\geq$constE11, $E11_i = E11\max(<1)$.

The step (A) may also be the step of computing, as the processing evaluation value $E1_i$ of an i-th base, an evaluation indicator $E12_i$ defined by the following formula:

$$E1_i = E12_i$$

where $E12_i$ is an evaluation indicator for evaluating a mobility correction amount (a, b, c) of measured data of an i-th base peak, and is represented by the following formula:

$$E12_i = (T(a1,b1,c1) - T(a2,b2,c2))/T(a1,b1,c1)$$

where T(a1, b1, c1) is a total peak area obtained by setting the mobility correction amount (a, b, c) to its best solution (a1, b1, c1), T(a2, b2, c2) is a total peak area obtained by setting the mobility correction amount (a, b, c) to its second best solution (a2, b2, c2), and when $$((T(a1,b1,c1)-T(a2,b2,c2))/T(a1,b1,c1)) > E12\max,$$
$$E12_i = E12\max(<1).$$

The step (A) may also be the step of computing, as the processing evaluation value $E1_i$ of an i-th base, an evaluation indicator $E11_i \times E12_i$ defined by the following formula:

$$E1_i = E11_i \times E12_i$$

where $E11_i$ is an evaluation indicator for evaluating a signal-to-noise ratio of measured data of an i-th base peak and is represented by the following formula:

$$E11_i = E11\max \times (\text{Signal}(i)/\text{Noise}(i))/\text{const}E11$$

where constE11 is a normalized constant and when (Signal (i)/Noise(i))$\geq$constE11, $E11_i = E11\max$; and $E12_i$ is an evaluation indicator for evaluating a mobility correction amount (a, b, c) of measured data of an i-th base peak, and is represented by the foil owing formula:

$$E12_i = (T(a1,b1,c1) - T(a2,b2,c2))/T(a1,b1,c1)$$

where T(a1, b1, c1) is a total peak area obtained by setting the mobility correction amount (a, b, c) to its best solution (a1, b1, c1), T(a2, b2, c2) is a total peak area obtained by setting the mobility correction amount (a, b, c) to its second best solution (a2, b2, c2), and when $$((T(a1,b1,c1)-T(a2,b2,c2))/T(a1,b1,c1)) > E12\max,$$
$$E12_i = E12\max(<1).$$

The step (B) may be the step of computing, as the analytical data evaluation value $E2_i$ of an i-th base, a characteristic indicator for evaluating peak-to-peak intervals of the analytical data represented by the following formula:

$$E2_i = d\text{Min}_i/d\text{Max}_i$$

where $d\text{Max}_i$ and $d\text{Min}_i$ are a maximum value and a minimum value, respectively, among values of an interval $d_{i(n)}$ between, two adjacent base peaks among a peak of the i-th base and base peaks near the peak of the i-th base, and when $(d\text{Min}_i/d\text{Max}_i) > E2\max$, $E2_i = E2\max(<1)$.

The step (B) may be the step of computing, as the analytical, data evaluation value $E2_i$ of an i-th base, a characteristic indicator for evaluating a signal-to-noise ratio of the analytical data represented by the following formula:

$$E2_i = E2\max(\text{Smin}_i/\text{Nmax}_i)/\text{Const}E2$$

where $\text{Smin}_i$ is a peak intensity of a minimum peak among a peak of the i-th base and base peaks near the peak of the i-th base, $\text{Nmax}_i$ is a peak intensity of a maximum noise peak among noise peaks present near the peak of the i-th base but not having teen identified as base peaks, ConstE2 is a normalized constant, and when $(\text{Smin}_i/\text{Nmax}_i) \geq \text{Const}E2$, $E2_i = E2\max$.

In this case, the peak intensity is a peak top height or a peak area.

Effects of the Invention

According to the present invention, since the degree of reliability is assessed using a processing evaluation value computed when measured data Is processed into analytical data, the quality of the measured data and the contents of processing having been performed on the measured data to obtain analytical data can be evaluated. Therefore, it is possible to obtain a higher-accuracy assessment result of the degree of reliability as compared to a case where the degree of reliability is assessed based on only the evaluation of analytical data according to a conventional method.

Further, unlike a conventional method, the method according to the present invention is simple because the degree of reliability is assessed by a predetermined calculation formula and, it is not necessary to collect data from many known samples. In addition, an emir of the degree of reliability resulting from the improperness of quality or quantity of the population of data collected from known samples is not caused in principle.

DESCRIPTION OF THE REFERENCE NUMERALS 12 waveform processing means
14 base sequence determining means

BEST MODE FOR CARRYING OUT THE INVENTION

Figure 1:
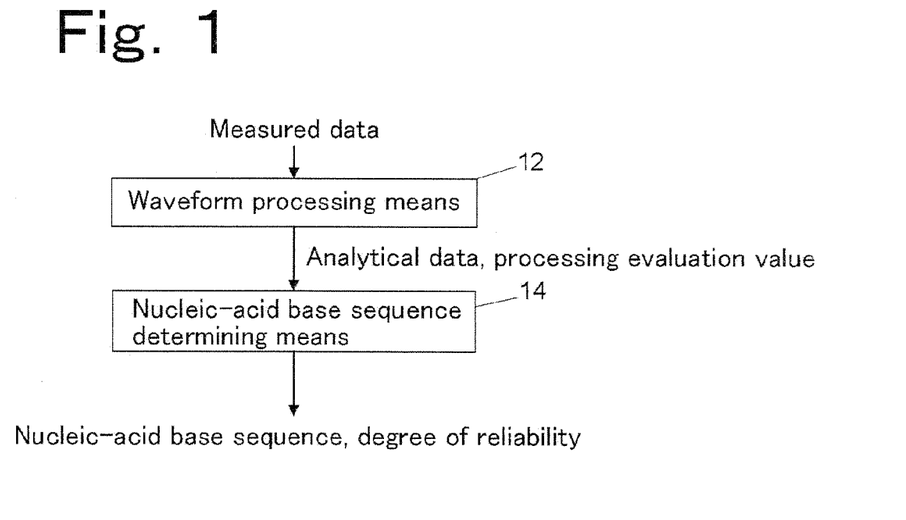
FIG. 1 is a block diagram schematically showing the functions of an apparatus for use in carrying out the present invention.
Figure 2:
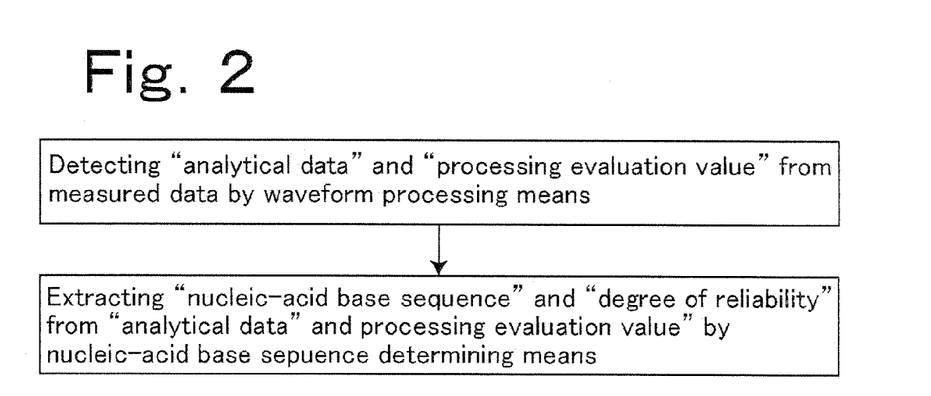
FIG. 2 is a flow chart showing one embodiment of the present invention.

FIG. 1 is a functional block diagram of a data processing computer for use in carrying out the present invention, and FIG. 2 is a flow chart of data processing carried out by the computer. Hereinbelow, one embodiment of the present invention will be described with reference to FIGS. 1 and 2.

Figure 3:
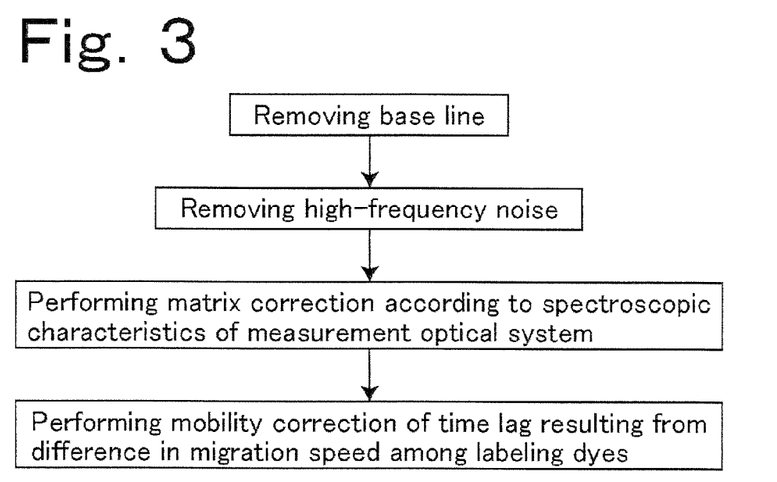
FIG. 3 is a flow chart of a waveform processing step of the embodiment shown in FIG. 2.
Figure 4:
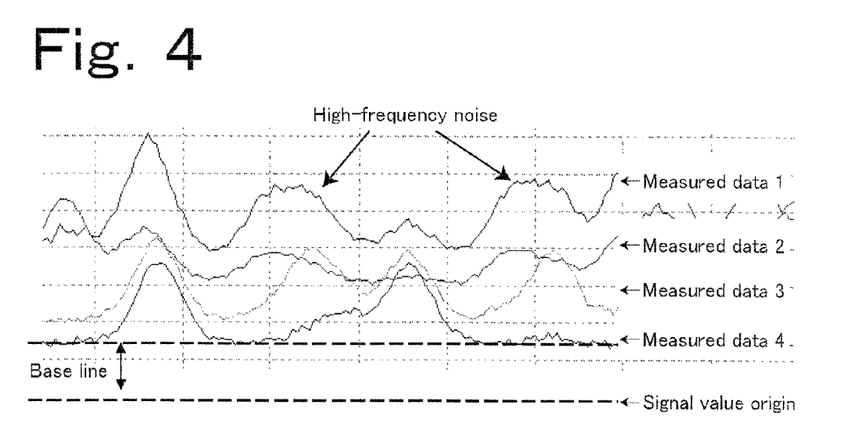
FIG. 4 is a graph showing the electrophoretic data of four kinds of bases.

First, measured data is processed by a waveform processing means 12 into "analytical data". In this processing step, a "processing evaluation value" is also computed. FIG. 3 is a flow chart showing an example of processing performed by the waveform processing means on the measured data. FIG. 4 is a graph showing examples of measured data obtained by electrophoretic measurement using labeling dyes.

Hereinbelow, examples of processing performed by the waveform processing means will be described with reference to FIGS. 3 and 4.

Four measured data sets 1, 2, 3, and 4 obtained by electrophoretic measurement using labeling dyes corresponding to four kinds of bases, A, G, C, and T are shown in FIG. 4 as examples of measured data. It is to be noted that, in some cases, the number of kinds of bases and the number of time-series signals are not always the same. In addition, the number of time-series signals is not limited to 4, mid the present invention is not intended to limit the number of time-series signals.

As shown in FIG. 4, each of the measured data sets generally has disturbing information, such as a base line and high-frequency noise, which makes it difficult to read information inherent in the signal. Therefore, in the case of measured-data processing shown in FIG. 3, disturbing information is first eliminated by removing a base line and high-frequency noise from each of the measured data sets. Removal of a base line and high-frequency noise can be achieved by using a method generally used for signal processing (see Non-Patent Document 2).

As such a general method for signal processing, for example, there is known a method in which measured data is transformed into frequency components by mathematical transformation used for frequency analysis such as Fourier transform or Wavelet transform, and then inverse transformation is performed after only certain frequency components are removed or reduced. More specifically, a base line is generally distributed into direct-current components or low-frequency components by transformation, and noise is generally distributed into high-frequency components by transformation. Further, the frequency properties of a measurement system are dependent to some degree on the measurement system used. Therefore, in the case of using this method distribution ranges of frequency components corresponding to a base line and high-frequency noise are previously determined, and frequency components corresponding to a base line and high-frequency noise are reduced or removed from frequency components obtained by transformation. Then, by performing inverse transformation, it is possible to obtain a signal waveform having no base line nor noise or a signal waveform having a reduced base line and reduced noise.

In the case of measured data obtained by electrophoresis using labeling dyes, signals having fluorescence intensity information of two or more kinds of bases are often superimposed on one another. Therefore, in the case of measured-data processing shown in FIG. 3, after disturbing information is removed from measured data, matrix correction is performed to separate them according to the spectrum characteristics of labeling dyes and the spectroscopic characteristics of a measurement optical system so that fluorescence intensity signals corresponding to four kinds of bases are obtained. The contents of processing for performing matrix correction are not particularly limited, but for example, a method described in Patent Document 1 can be used.

The method described in Patent Document 1 is based on a fluorescence dye terminator labeling method using two or more fluorescence dyes having different fluorescent wavelengths. More specifically, signal waveforms of bases are determined by performing matrix transformation on waveform signals obtained from detection units different depending on the kind of fluorescence dye, and then base sequence determination is performed based on the signal waveforms. In this case, a matrix value for performing matrix transformation is obtained from actual sample migration by perforating the following steps in order:

(A) extracting peaks from a proper range;
(B) eliminating peaks occulting at irregular intervals;
(C) classifying peak groups containing signals of four kinds of bases, A, G, C and T into four groups corresponding to the four kinds of bases based on signal intensity;
(D) determining the signal intensity ratios among A, G, C, and T of the four classified groups;
(E) assigning the corresponding bases to the four classified groups; and
(F) obtaining a matrix value from the signal intensity ratios of peak waveforms of the respective base groups.

Further, a time lag often occurs among time-series signals having fluorescence intensity information due to a difference in migration speed among labeling dyes. In the case of measured-data processing shown in FIG. 3, mobility correction is performed to correct a time lag among fluorescence intensity signals of four kinds of bases resulting from a difference in migration speed among labeling dyes.

The contents of processing for performing mobility correction are not particularly limited, but for example, a method described in Patent Document 2 can be used.

The method described in Patent Document 2 includes, as preprocessing for determining a nucleic acid base sequence based on detection data obtained by electrophoresing a nucleic acid fragment sample, the step of shifting the detection data. In the detection data shifting step, four kinds of detection data sets corresponding to four kinds of bases are superimposed on one another, and then one to three kinds of the four kinds of detection data sets are fixed and the remaining detection data set(s) is (are) shifted in the forward and backward direction to determine the shift amount(s) of the detection data set(s) so that the total area of a peak waveform becomes maximum.

The method described in Patent Document 2 will be described in more detail below. Four detection data sets corresponding to the four kinds of bases are obtained, and then the detection data set(s) of a reference base(s) previously determined is (are) defined as a reference detection data set(s). Then, the detection data set(s) other than the reference detection data set(s) is (are) shifted, and the total area of a peak waveform is computed. A linear shift is employed as a function for mobility correction to determine the shift amount(s) of the detection data set(s) other than the reference detection data set(s) so that the total area of a peak waveform becomes maximum, and then the positional information of the detection data set(s) is corrected based on the shift amount(s), Then, a temporary base sequence is determined, and the detection data set(s) of the reference base(s) is (are) defined as reference detection data set(s), and an object peak, before and after which reference peaks of the reference detection data set(s) are present, is selected from each detection data set other than the reference detection data set(s). The peak-to-peak interval between the object peak and the reference peak present before the object peak and the peak-to-peak interval between the object peak and the reference peak present after the object peak are determined, and the shift amount of the object peak required to equalize these peak-to-peak intervals is computed. The positional information of the detection data, to which the object peak belongs, is corrected based on the shift amount of the object peak.

Figure 5:
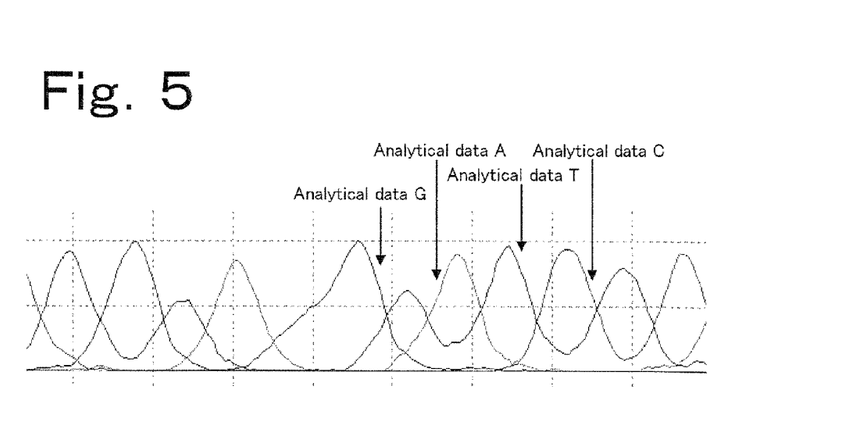
FIG. 5 is a graph showing electrophoretic analytical data obtained by performing waveform processing on the electrophoretic data shown in FIG. 4.

FIG. 5 is a graph showing an example of "analytical data" obtained by performing processing shown in FIG. 3 on the measured data shown in FIG. 4. In FIG. 5, four analytical data sets A, G, C, and T show a change in fluorescence intensity with time of the four kinds of bases A, G, C, and T, respectively. As shown in FIG. 5, base peaks are spaced at substantially equal intervals on the "analytical data", and a base sequence is determined by identifying these base peaks.

The degree of reliability of each base of the determined base sequence (=the probability that the identification of each base is reliable) can be estimated by calculating the characteristic indicator of the analytical data by the use of information obtained from the analytical data such as the intervals between adjacent two base peaks among a base peak as a target of assessment of the degree of reliability and base peaks near the target base peak and the amplitudes of noise peaks other than base peaks.

Figure 6:
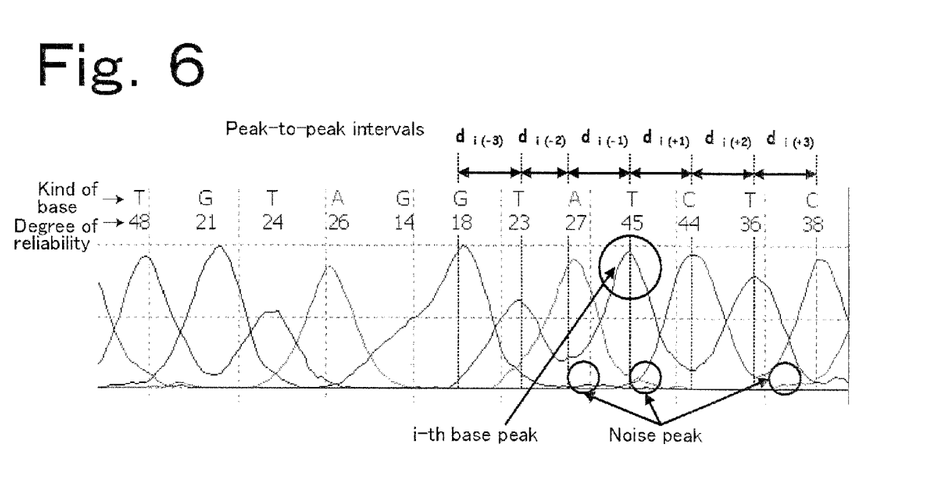
FIG. 6 is a graph showing an example of a nucleic acid base sequence determined based on the analytical data and an example of assessment of the degree of reliability.

FIG. 6 shows an example of abase sequence determined based on the analytical data shown in FIG. 5 and examples of the degree of reliability assessed by a method which will be described later. Further, FIG. 6 shows the interval $d_{i(n)}$ ($n=\pm 1, \pm 2, \ldots$) between base peaks present around an i-th base peak and examples of a noise peak.

For example, when a maximum value and a minimum value among the values of the interval $d_{i(n)}$ between two adjacent base peaks among an i-th base peak and 6 base peaks around the i-th base peak (i.e., $n=\pm 3$) are defined as $dMax_i$ and $dMin_i$, respectively, a characteristic indicator $E21_i$ for evaluating the peak-to-peak interval of the analytical data is defined as an analytical data evaluation value $E2_i$ and calculated by the following formula:

$$E21_i = dMin_i/dMax_i$$

whereiwhen $(dMini/dMaxi) > E21\max, E21_i = E21\max$
(<1) \hfill (2)

Here, E21max is defined as an accuracy rate at the time when the reliability of the evaluation value is maximum, and is a constant less than 1. For example, E21max can be set to 0.999999. As in the case of E21max, E22max, E11max, and E12max, which will be described later, are also each defined as an accuracy rate at the time when the reliability of respective evaluation values is maximum. E21max, E22max, E11max, and E12max may be the same value Emax or different from each other as long as they are less than 1.

$E21_i$ takes a value between 0 and E21max, and $E21_i$ closer to E21max (<1) leads to the estimate that reliability is higher. This is based on the well-known findings that more highly-reliable analytical data is characterized in that base peaks are spaced at more regular intervals, which is described also in Non-Patent Document 1.

Further, when the peak intensity (peak top height and/or peak area) of a minimum peak among an i-th base peak and 6 base peaks around the i-th base peak (3 peaks before and 3 peaks after the i-th base peak) is defined as $Smin_i$ and the peak intensity of a maximum noise peak among noise peaks (=peaks not identified as base peaks) present in the analytical data within a range containing the above 7 base peaks is defined as $Nmax_i$, a characteristic indicator $E22_i$ for evaluating the signal-to-noise ratio of the analytical data is defined as an analytical data evaluation value $E2_i$ and is calculated by the following formula using a normalized constant ConstE22:

$$E22_i = E22\max \times (Smin_i/Nmax_i)/ConstE22$$

where when $(Smin_i/Nmax_i) \geq ConstE22$,
$E22_i = E22\max (<1)$ \hfill (3)

ConstE22 has the meaning of a threshold value for the value of $(Smin_i/Nmax_i)$. When the value of $(Smin_i/Nmax_i)$ is equal to or more than a threshold value ConstE22, $E22_i$ takes a maximum value E22max. On the other hand, when the value of $(Smin_i/Nmax_i)$ is less than a threshold value ConstE22, $E22_i$ takes a value between 0 and E22max. ConstE22 is previously and empirically determined. For example, in a case where $E22_i$ takes a maximum value E22max at the time when the value of $(Smin_i/Nmax_i)$ is larger than 10, ConstE22 is defined as 10.

As described above, $E22_i$ takes a value between 0 and E22max. $E22_i$ closer to E22max(<1) leads to the estimate that reliability is higher. This is based on the well-known findings that more highly-reliable analytical data is characterized in that base peaks are larger and noise peaks are smaller, which is described also in Non-Patent Document 1.

However, the degree of reliability of each identified base cannot be accurately assessed simply by evaluating the above-described characteristic indicators obtained from "analytical data". This is because, although these characteristic indicators are tools for evaluating the quality of "analytical data", the degree of reliability of each identified base greatly depends on the quality of measured data that is the original of "analytical data" and the contents of processing having been performed on the measured data to obtain "analytical data".

The present invention is characterized in that a method for evaluating the quality of measured data and the contents of processing having been performed on the measured data to obtain "analytical data" is defined as "processing evaluation value" and obtained by calculation, and the obtained processing evaluation value is used together with the characteristic indicators obtained from "analytical data" to assess the degree of reliability of each base.

Hereinbelow, examples of "processing evaluation value" will be described.

For example, prior to processing of measured data, the noise amplitude value Noise(i) and signal amplitude value Signal(i) of measured data within a time interval $\Delta t$ before and after a peak i (i.e., an i-th base peak) are determined, and then an evaluation indicator $E11_i$ for evaluating the signal-to-noise ratio of the measured data defined as a processing evaluation value $E1_i$ is calculated by the following formula using a normalized constant constE11:

$$E11_i = E11\max \times (\text{Signal}(i)/\text{Noise}(i))/\text{const}E11$$

where when $\text{Signal}(i)/\text{Noise}(i) \geq \text{const}E11$,
$$E11_i = E11\max(<1) \quad (4)$$

$E11_i$ takes a value between 0 and E11max, and $E11_i$ closer to E11max ($<1$) means that the measured data of the peak i has higher quality. Tire normalized constant constE11 has the meaning of a threshold value for the value of (Signal(i)/Noise(i)).

Here, since the horizontal axis of the measured data is a temporal axis, the time interval $\Delta t$ before and after the i-th base peak actually includes the peak top time $t_i$ of the i-th base peak.

The mobility correction described above as part of measured-data processing is performed using a mobility correction amount obtained by calculation. In this case, an evaluation indicator for the probability that a mobility correction amount obtained by calculation is reliable can be determined. For example, when the peak position of the base G is fixed, and the peak positions of the other bases A, T, and C are shifted by the amounts of a, b, and c, respectively according to the method described in Patent Document 2 so that a correction amount is defined as (a, b, c), the best solution of (a, b, c) is determined based on the findings that a preferred mobility correction amount can be achieved by avoiding overlap between peaks so that the total peak area T(a, b, c) becomes larger. In this case, an evaluation indicator E12 is defined as a processing evaluation value E1 and calculated by the following formula using the total peak area T(a1, b1, c1) achieved by the best solution (a1, b1, c1) and the total peak area T(a2, b2, c2) achieved by the second best solution (a2, b2, c2):

$$E12 = (T(a1,b1,c1) - T(a2,b2,c2))/T(a1,b1,c1)$$

where when $(T(a1,b1,c1) - T(a2,b2,c2))/T(a1,b1,c1) >$
$E12\max, E12 = E12\max(<1)$ (5)

E12 takes a value between 0 and E12max, and E12 closer to E12max ($<1$) means that the best solution (a1, b1, c1) is a more definitive mobility correction amount and therefore the possibility that mobility correction is achieved by another mobility correction amount is lower. On the other hand, E12 closer to 0 means that the best solution (a1, b1, c1) is a more uncertain mobility correction amount and therefore the possibility that mobility correction is achieved by another mobility correction amount is higher. It is to be noted that in a case where the mobility correction amount is determined as an amount that changes with time, E12 is obtained every time when a base peak appears, that is, E12 is obtained at the peak top time of each base peak. Therefore, E12 is hereinafter referred to as a more general value $E12_i$.

Further, the present invention is characterized also in that the degree of reliability of a nucleic acid base sequence is assessed by a predetermined calculation formula using the "analytical data evaluation value" and the "processing evaluation value".

The degree of reliability $QV_i$ of an i-th base peak is assessed by, for example, the following formula:

$$QV_i = -\text{const}QV \times \log_{10}(\text{Err}_i) \quad (6)$$

Here, constQV is a correction constant and is previously set to an appropriate value so that a value quantitatively corresponding to the reliability degree value defined by the above-described formula (1) using an error probability estimated from actual error rates can be obtained by the formula (6).

$\text{Err}_i$ is an error probability of an i-th base, and is defined using at least one "analytical data evaluation value" selected from evaluation values defined by, for example, the formulas (2) and (3) and at least one "processing evaluation value" selected from evaluation values defined by, for example, the formulas (4) and (5).

More specifically, $\text{Err}_i$ is defined by, for example, the following formula:

$$\text{Err}_i = (1 - E2_i) \times (1 - E1_i) \quad (7)$$

Here, $E2_i$ may be either $E21_i$ or $E22_i$. Alternatively, $E2_i$ may be $E21_i \times E22_i$.

$E1_i$ may be either $E11_i$ or $E12_i$. Alternatively, $E1_i$ may be $E11_i \times E12_i$.

When the evaluation values $E2_i$ and $E1_i$ in the formula (7) are each closer to 1, the error probability $\text{Err}_i$ is closer to 0, that is, the degree of reliability is higher. On the other hand, when the evaluation values $E2_i$ and $E1_i$ in the formula (7) are each closer to 0, the error probability $\text{Err}_i$ is closer to 1.

The evaluation values $E2_i$ and $E1_i$ used for determining the error probability $\text{Err}_i$ are not limited to those defined by the formulas (2) to (5). The "analytical data evaluation value" $E2_i$ can be appropriately selected by those skilled in the art from dimensionless characteristic indicators taking a value of 0 to less than 1 for evaluating the quality of analytical data. The "processing evaluation value" $E1_i$ can also be appropriately selected by those skilled in the art from dimensionless characteristic indicators taking a value of 0 to less than 1 for evaluating the quality of measured data or the contents of processing having been performed on the measured data to obtain "analytical data".

As described above, the degree of reliability of a nucleic acid base sequence can be assessed by inputting at least one "analytical data evaluation value" defined by, for example, the formula (2) or (3) and at least one "processing evaluation value" defined by, for example, the formula (4) or (5) into the predetermined calculation formulas defined by, for example, the formulas (6) and (7). It is to be noted that the values shown as "degree of reliability" in FIG. 6 were determined using the formula (6).

It is to be noted that in the above embodiment, evaluation values defined by the formulas (2) to (5) are used as the "analytical data evaluation values" and the "processing evaluation values", but the "analytical data evaluation value" and the "processing evaluation value" are not limited thereto, and other function forms may be used.

Figure 7:
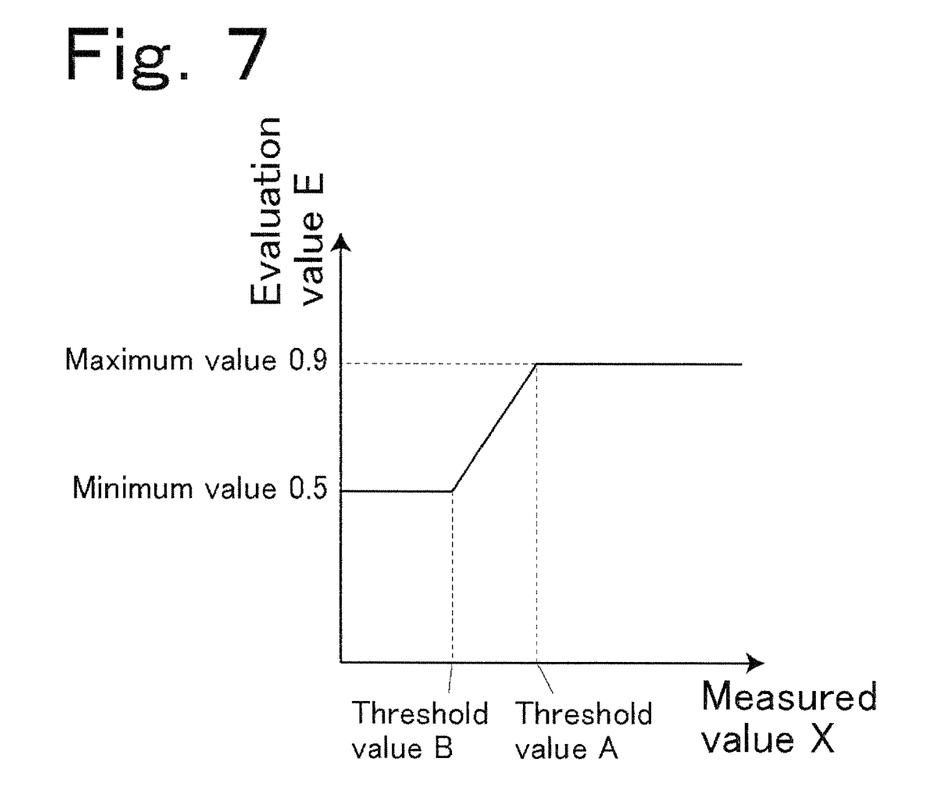
FIG. 7 is a graph showing one example of a functional form for computing an evaluation value E.

FIG. 7 shows the functional form of each evaluation value E. For example, in the case of the processing evaluation value $E21_i$, the horizontal axis represents a measured value X of the SN ratio of measured data. When the horizontal axis value X is larger than a predetermined threshold value A, the evaluation value E always takes a maximum value Emax. The reliability of determination of a nucleic acid base sequence is higher when all the evaluation values reach a certain level than when only a certain evaluation value is remarkably large. Therefore, the use of such a functional form makes it possible to realize a method for assessing the degree of reliability in which when a certain evaluation value is larger than a certain level, the degree of reliability is determined by one or more other evaluation values regardless of how large the certain evaluation value is. This assessment method is effective at reflecting the above-described characteristics of the reliability of determination of a nucleic acid base sequence.

More preferably, as shown in FIG. 7, the functional form of each evaluation value E is set so that the evaluation value E always takes a minimum value Emin when the horizontal axis value X is smaller than a predetermined threshold value B. By providing the minimum value Emin, it is possible to, even when a certain evaluation value is remarkably small, keep the contribution of one or more other evaluation values to prevent the degree of reliability from being reduced more than necessary, thereby enabling the reliability degree value to be determined. This is advantageous to determination of a nucleic acid base sequence.

In a case where an attempt to assess one indicator value (in the present invention, the reliability degree value) using two or more evaluation values having different physical origins is made, it is difficult to strike a balance among these evaluation values. However, by previously regulating the saturation characteristics of all the evaluation values using the evaluation value calculation methods represented by the formulas (2) to (5) according to this embodiment and the functional form shown in FIG. 7, it is possible to appropriately control a balance among the evaluation values so that the influence of a certain evaluation value on overall evaluation does not become too large or too small relative to one or more other evaluation values. This is effective at creating an assessment formula by which the degree of reliability can be assessed with higher accuracy because a prior knowledge information about two or more factors can be expressed as two or more evaluation values having different physical origins and can be more accurately used.

Further, according to the method for assessing the degree of reliability using the evaluation values and the formulas (6) and (7) described with reference to the above embodiment the evaluation values each taking a value of 0 to less than 1 are converted by the formula (7) into a value corresponding to a principled error probability, and then the principled error probability is converted by a functional form represented by the formula (6) close to the formula (1) into a reliability degree value. Therefore, it is possible to assess the reliability degree value principally corresponding to the reliability degree value correlated with the error probability and represented by the formula (1).

What is claimed is:

1. A method for assessing the degree of reliability of a nucleic acid base sequence, comprising the steps of:
   (A) computing a processing evaluation value $E1_i$ for evaluating quality of measured data of an i-th base and/or contents of processing having been performed on the measured data of the i-th base when the measured data is processed into analytical data;
   (B) computing an analytical data evaluation value $E2_i$ of the i-th base based on the processed analytical data; and
   (C) computing a degree of reliability by a predetermined calculation formula using the processing evaluation value $E1_i$ and the analytical data evaluation value $E2_i$,
   wherein steps (A)-(C) are performed by a data processing computer,
   wherein in the step (A), an evaluation indicator $E11_i$ defined by the following formula is computed as the processing evaluation value $E1_i$ of an i-th base:

$$E1_i = E11_i$$

where $E11_i$ is an evaluation indicator for evaluating a signal-to-noise ratio of measured data of an i-th base peak and is represented by the following formula:

$$E11_i = E11\text{max} \times (\text{Signal}(i)/\text{Noise}(i)/\text{const}E11$$

where constE11 is a normalized constant, and when (Signal(i)/Noise(i))≧constE11, $E11_i = E11\text{max}(<1)$,
   wherein in the step (B), a characteristic indicator for evaluating a peak-to-peak interval of the analytical data defined by the following formula is computed as the analytical data evaluation value $E2_i$ of an i-th base:

$$E2_i = d\text{Min}_i/d\text{Max}_i$$

where $d\text{Max}_i$ and $d\text{Mini}$ are a maximum value and a minimum value, respectively, among values of an interval $d_{i(n)}$ between two adjacent base peaks among a peak of the i-th base and base peaks near the peak of the i-th base, and when $(d\text{Min}_i/d\text{Max}_i) > E2\text{max}$, $E2_i = E2\text{max}(<1)$, and
   wherein in the step (C), a degree of reliability $QV_i$ of an i-th base peak is computed by the following calculation formula:

$$QV_i = \text{const}QV \times \text{Log}_{10}(\text{Err}_i)$$

where constQV is a correction constant and $\text{Err}_i$ is an error probability of an i-th base and is represented by the following formula:

$$\text{Err}_i = -(1-E1_i) \times (1-E2_i)$$

where $E1_i$ and $E2_i$ each takes a value between 0 and 1 and has Emax which is a maximum value less than 1.

2. The method for assessing the degree of reliability according to claim 1,
   wherein the data processing computer comprises a waveform processing means for processing the measured data to obtain analytical data and a base sequence determining means, the waveform processing means performing at least a matrix correction to separate fluorescence intensity signals of two or more kinds of bases to each other based on spectrum characteristics of labeling dyes and spectroscopic characteristics of a measurement optical system, and a mobility correction to correct a time lag among fluorescence intensity signals of two or more kinds of bases resulting from a difference in migration speed among labeling dyes,
   wherein the contents of processing and the processed analytical data are obtained by the waveform processing means, and
   wherein the base sequence determining means outputs determined base sequence with a calculated degree of reliability for each base of the determined base sequence.

3. A method for assessing the degree of reliability of a nucleic acid base sequence, comprising the steps of:
   (A) computing a processing evaluation value $E1_i$ for evaluating quality of measured data of an i-th base and/or contents of processing having been performed on the measured data of the i-th base when the measured data is processed into analytical data;
   (B) computing an analytical data evaluation value $E2_i$ of the i-th base based on the processed analytical data; and
   (C) computing a degree of reliability by a predetermined calculation formula using the processing evaluation value $E1_i$ and the analytical data evaluation value $E2_i$,
   wherein steps (A)-(C) are performed by a data processing computer,
   wherein in the step (A), an evaluation indicator $E11_i$ defined by the following formula is computed as the processing evaluation value $E1_i$ of an i-th base:

$$E1_i = E11_i$$

where $E11_i$ is an evaluation indicator for evaluating a signal-to-noise ratio of measured data of an i-th base peak and is represented by the following formula:

$$E11_i = E11\text{max} \times (\text{Signal}(i)/\text{Noise}(i))/\text{const}E11$$

where constE11 is a normalized constant, and when (Signal(i)/Noise(i))≧constE11, $E11_i = E11\text{max}(<1)$, wherein in the step (B), a characteristic indicator for evaluating a signal-to-noise ratio of the analytical data defined by the following formula is computed as the analytical data evaluation value $E2_i$ of an i-th base:

$$E2_i = E2\max \times (Smin_i/Nmax_i)/ConstE2$$

where $Smin_i$ is a peak intensity of a minimum peak among a peak of the i-th base and base peaks near the peak of the i-th base, $Nmax_i$ is a peak intensity of a maximum noise peak among noise peaks present near the peak of the i-th base but not having been identified as base peaks, ConstE2 is a normalized constant, and when $(Smin_i/Nmax_i) \geq ConstE2$, $E2_i = E2\max$, and wherein in the step (C), a degree of reliability $QV_i$ of an i-th base peak is computed by the following calculation formula:

$$QV_i = -constQV \times \log_{10}(Err_i)$$

where constQV is a correction constant and $Err_i$ is an error probability of an i-th base and is represented by the following formula:

$$Err_i = (1 - E1_i) \times (1 - E2_i)$$

where $E1_i$ and $E2_i$ each takes a value between 0 and 1 and has Emax which is a maximum value less than 1.

4. The method for assessing the degree of reliability according to claim 3,
wherein the data processing computer comprises a waveform processing means for processing the measured data to obtain analytical data and a base sequence determining means, the waveform processing means performing at least a matrix correction to separate fluorescence intensity signals of two or more kinds of bases to each other based on spectrum characteristics of labeling dyes and spectroscopic characteristics of a measurement optical system, and a mobility correction to correct a time lag among fluorescence intensity signals of two or more kinds of bases resulting from a difference in migration speed among labeling dyes,
wherein the contents of processing and the processed analytical data are obtained by the waveform processing means, and
wherein the base sequence determining means outputs determined base sequence with a calculated degree of reliability for each base of the determined base sequence.

5. A method for assessing the degree of reliability of a nucleic acid base sequence, comprising the steps of
(A) computing a processing evaluation value $E1_i$ for evaluating quality of measured data of an i-th base and/or contents of processing having been performed on the measured data of the i-th base when the measured data is processed into analytical data;
(B) computing an analytical data evaluation value $E2_i$ of the i-th base based on the processed analytical data; and
(C) computing a degree of reliability by a predetermined calculation formula using the processing evaluation value $E1_i$ and the analytical data evaluation value $E2_i$,
wherein steps (A)-(C) are performed by a data processing computer,
wherein in the step (A), an evaluation indicator $E12_i$ defined by the following formula is computed as the processing evaluation value $E1_i$ of an i-th base:

$$E1_i = E12_i$$

where $E12_i$ is an evaluation indicator for evaluating a mobility correction amount (a, b, c) of measured data of an i-th base peak and is represented by the following formula:

$$E12_i = (T(a1,b1,c1) - T(a2,b2,c2))/T(a1,b1,c1)$$

where $T(a1, b1, c1)$ is a total peak area obtained by setting the mobility correction amount (a, b, c) to its best solution (a1, b1, c1), $T(a2, b2, c2)$ is a total peak area obtained by setting the mobility correction amount (a, b, c) to its second best solution (a2, b2, c2), and when $((T(a1, b1, c1) - T(a2, b2, c2))/T(a1, b1, c1)) > E12\max$, $E12_i = E12\max (<1)$, wherein in the step (B), a characteristic indicator for evaluating a peak-to-peak interval of the analytical data defined by the following formula is computed as the analytical data evaluation value $E2_i$ of an i-th base:

$$E2_i = dMin_i/dMax_i$$

where $dMax_i$ and $dMin_i$ are a maximum value and a minimum value, respectively, among values of an interval $d_{i(n)}$ between two adjacent base peaks among a peak of the i-th base and base peaks near the peak of the i-th base, and when $(dMin_i/dmax_i) > E2\max$, $E2_i = E2\max(<1)$, and wherein in the step (C), a degree of reliability $QV_i$ of an i-th base peak is computed by the following calculation formula:

$$QV_i = -constQV \times \log_{10}(Err_i)$$

where constQV is a correction constant and $Err_i$ is an error probability of an i-th base and is represented by the following formula:

$$Err_i = (1 - E1_i) \times (1 - E2_i)$$

where $E1_i$ and $E2_i$ each takes a value between 0 and 1 and has Emax which is a maximum value less than 1.

6. The method for assessing the degree of reliability according to claim 5,
wherein the data processing computer comprises a waveform processing means for processing the measured data to obtain analytical data and a base sequence determining means, the waveform processing means performing at least a matrix correction to separate fluorescence intensity signals of two or more kinds of bases to each other based on spectrum characteristics of labeling dyes and spectroscopic characteristics of a measurement optical system, and a mobility correction to correct a time lag among fluorescence intensity signals of two or more kinds of bases resulting from a difference in migration speed among labeling dyes,
wherein the contents of processing and the processed analytical data are obtained by the waveform processing means, and
wherein the base sequence determining means outputs determined base sequence with a calculated degree of reliability for each base of the determined base sequence.

7. A method for assessing the degree of reliability of a nucleic acid base sequence, comprising the steps of:
(A) computing a processing evaluation value $E1_i$ for evaluating quality of measured data of an i-th base and/or contents of processing having been performed on the measured data of the i-th base when the measured data is processed into analytical data;
(B) computing an analytical data evaluation value $E2_i$ of the i-th base based on the processed analytical data; and (C) computing a degree of reliability by a predetermined calculation formula using the processing evaluation value $E1_i$ and the analytical data evaluation value $E2_i$, wherein steps (A)-(C) are performed by a data processing computer, wherein in the step (A), an evaluation indicator $E12_i$ defined by the following formula is computed as the processing evaluation value $E1_i$ of an i-th base:

$$E1_i = E12_i$$

where $E12_i$ is an evaluation indicator for evaluating a mobility correction amount (a, b, c) of measured data of an i-th base peak and is represented by the following formula:

$$E12_i = (T(a1,b1,c1) - T(a2,b2,c2))/T(a1,b1,c1)$$

where T(a1, b1, c1) is a total peak area obtained by setting the mobility correction amount (a, b, c) to its best solution (a1, b1, c1), T(a2, b2, c2) is a total peak area obtained by setting the mobility correction amount (a, b, c) to its second best solution (a2, b2, c2), and when $((T(a1, b1, c1) - T(a2, b2, c2))/T(a1, b1, c1)) > E12max$, $E12_i = E12max (<1)$, wherein in the step (B), a characteristic indicator for evaluating a signal-to-noise ratio of the analytical data defined by the following formula is computed as the analytical data evaluation value $E2_i$ of an i-th base:

$$E2_i = E2max \times (Smin_i/Nmax_i)/ConstE2$$

where $Smin_i$ is a peak intensity of a minimum peak among a peak of the i-th base and base peaks near the peak of the i-th base, $Nmax_i$ is a peak intensity of a maximum noise peak among noise peaks present near the peak of the i-th base but not having been identified as base peaks, ConstE2 is a normalized constant, and when $(Smin_i/Nmax_i)$ ConstE2, $E2_i = E2max$, and wherein in the step (C), a degree of reliability $QV_i$ of an i-th base peak is computed by the following calculation formula:

$$QV_i = -constQV \times Log_{10}(Err_i)$$

where constQV is a correction constant and $Err_i$ is an error probability of an i-th base and is represented by the following formula:

$$Err_i = (1-E1_i) \times (1-E2_i)$$

where $E1_i$ and $E2_i$ each takes a value between 0 and 1 and has Emax which is a maximum value less than 1.

8. The method for assessing the degree of reliability according to claim 7, wherein the data processing computer comprises a waveform processing means for processing the measured data to obtain analytical data and a base sequence determining means, the waveform processing means performing at least a matrix correction to separate fluorescence intensity signals of two or more kinds of bases to each other based on spectrum characteristics of labeling dyes and spectroscopic characteristics of a measurement optical system, and a mobility correction to correct a time lag among fluorescence intensity signals of two or more kinds of bases resulting from a difference in migration speed among labeling dyes, wherein the contents of processing and the processed analytical data are obtained by the waveform processing means, and wherein the base sequence determining means outputs determined base sequence with a calculated degree of reliability for each base of the determined base sequence.

9. A method for assessing the degree of reliability of a nucleic acid base sequence, comprising the steps of:

(A) computing a processing evaluation value $E1_i$ for evaluating quality of measured data of an i-th base and/or contents of processing having been performed on the measured data of the i-th base when the measured data is processed into analytical data;

(B) computing an analytical data evaluation value $E2_i$ of the i-th base based on the processed analytical data; and (C) computing a degree of reliability by a predetermined calculation formula using the processing evaluation value $E1_i$ and the analytical data evaluation value $E2_i$, wherein steps (A)-(C) are performed by a data processing computer, wherein in the step (A), an evaluation indicator $E11_i \times E12_i$ defined by the following formula is computed as the processing evaluation value $E1_i$ of an i-th base:

$$E1_i = E11_i \times E12_i$$

where $E11_i$ is an evaluation indicator for evaluating a signal-to-noise ratio of measured data of an i-th base peak and is represented by the following formula:

$$E11_i = E11max \times (Signal(i)/Noise(i))/constE11$$

where constE11 is a normalized constant and when $(Signal(i)/Noise(i)) \geq constE11$, $E11_i = E11max$; and $E12_i$ is an evaluation indicator for evaluating a mobility correction amount (a, b, c) of measured data of an i-th base peak and is represented by the following formula:

$$E12_i = (T(a1,b1,c1) - T(a2,b2,c2))/T(a1,b1,c1)$$

where T(a1, b1, c1) is a total peak area obtained by setting the mobility correction amount (a, b, c) to its best solution (a1, b1, c1), T(a2, b2, c2) is a total peak area obtained by setting the mobility correction amount (a, b, c) to its second best solution (a2, b2, c2), and when $((T(a1, b1, c1) - T(a2, b2, c2))/T(a1, b1, c1)) > E12max$, $E12_i = E12max (<1)$, wherein in the step (B), a characteristic indicator for evaluating a peak-to-peak interval of the analytical data defined by the following formula is computed as the analytical data evaluation value $E2_i$ of an i-th base:

$$E2_i = dMin_i/dMax_i$$

where $dMax_i$ and $dMin_i$ are a maximum value and a minimum value, respectively, among values of an interval $d_{i(n)}$ between two adjacent base peaks among a peak of the i-th base and base peaks near the peak of the i-th base, and when $(dMin_i/dMax_i) > E2max$, $E2_i = E2max (<1)$, and wherein in the step (C), a degree of reliability $QV_i$ of an i-th base peak is computed by the following calculation formula:

$$QV_i = -constQV \times Log_{10}(Err_i)$$

where constQV is a correction constant and $Err_i$ is an error probability of an i-th base and is represented by the following formula:

$$Err_i = (1-E1_i) \times (1-E2_i)$$

where $E1_i$ and $E2_i$ each takes a value between 0 and 1 and has Emax which is a maximum value less than 1.

10. The method for assessing the degree of reliability according to claim 9, wherein the data processing computer comprises a waveform processing means for processing the measured data to obtain analytical data and a base sequence determining means, the waveform processing means performing at least a matrix correction to separate fluorescence intensity signals of two or more kinds of bases to each other based on spectrum characteristics of labeling dyes and spectroscopic characteristics of a measurement optical system, and a mobility correction to correct a time lag among fluorescence intensity signals of two or more kinds of bases resulting from a difference in migration speed among labeling dyes, wherein the contents of processing and the processed analytical data are obtained by the waveform processing means, and wherein the base sequence determining means outputs determined base sequence with a calculated degree of reliability for each base of the determined base sequence.

11. A method for assessing the degree of reliability of a nucleic acid base sequence, comprising the steps of:

(A) computing a processing evaluation value $E1_i$ for evaluating quality of measured data of an i-th base and/or contents of processing having been performed on the measured data of the i-th base when the measured data is processed into analytical data;

(B) computing an analytical data evaluation value $E2_i$ of the i-th base based on the processed analytical data; and (C) computing a degree of reliability by a predetermined calculation formula using the processing evaluation value $E1_i$ and the analytical data evaluation value $E2_i$, wherein steps (A)-(C) are performed by a data processing computer, wherein in the step (A), an evaluation indicator $E11_i \times E12_i$ defined by the following formula is computed as the processing evaluation value $E1_i$ of an i-th base:

$$E1_i = E11_i \times E12_i$$

where $E11_i$ is an evaluation indicator for evaluating a signal-to-noise ratio of measured data of an i-th base peak and is represented by the following formula:

$$E11_i = E11\max \times (\text{Signal}(i)/\text{Noise}(i))/\text{const}E11$$

where constE11 is a normalized constant and when (Signal(i)/Noise(i))$\geq$constE11, $E11_i = E11\max$; and $E12_i$ is an evaluation indicator for evaluating a mobility correction amount (a, b, c) of measured data of an i-th base peak and is represented by the following formula:

$$E12_i = (T(a1,b1,c1) - T(a2,b2,c2))/T(a1,b1,c1)$$

where T(a1, b1, c1) is a total peak area obtained by setting the mobility correction amount (a, b, c) to its best solution (a1, b1, c1), T(a2, b2, c2) is a total peak area obtained by setting the mobility correction amount (a, b, c) to its second best solution (a2, b2, c2), and when ((T(a1, b1, c1)−T(a2, b2, c2))/T(a1, b1, c1))>E12max, $E12_i = E12\max(<1)$, wherein in the step (B), a characteristic indicator for evaluating a signal-to-noise ratio of the analytical data defined by the following formula is computed as the analytical data evaluation value $E2_i$ of an i-th base:

$$E2_i = E2\max \times (\text{Smin}_i/\text{Nmax}_i)/\text{Const}E2$$

where $\text{Smin}_i$ is a peak intensity of a minimum peak among a peak of the i-th base and base peaks near the peak of the i-th base, $\text{Nmax}_i$ is a peak intensity of a maximum noise peak among noise peaks present near the peak of the i-th base but not having been identified as base peaks, ConstE2 is a normalized constant, and when $(\text{Smin}_i/\text{Nmax}_i) \geq \text{Const}E2$, $E2_i = E2\max$, and wherein in the step (C), a degree of reliability $QV_i$ of an i-th base peak is computed by the following calculation formula:

$$QV_i = -\text{const}QV \times \text{Log}_{10}(\text{Err}_i)$$

where constQV is a correction constant and $\text{Err}_i$ is an error probability of an i-th base and is represented by the following formula:

$$\text{Err}_i = (1 - E1_i) \times (1 - E2_i)$$

where $E1_i$ and $E2_i$ each takes a value between 0 and 1 and has Emax which is a maximum value less than 1.

12. The method for assessing the degree of reliability according to claim 11, wherein the data processing computer comprises a waveform processing means for processing the measured data to obtain analytical data and a base sequence determining means, the waveform processing means performing at least a matrix correction to separate fluorescence intensity signals of two or more kinds of bases to each other based on spectrum characteristics of labeling dyes and spectroscopic characteristics of a measurement optical system, and a mobility correction to correct a time lag among fluorescence intensity signals of two or more kinds of bases resulting from a difference in migration speed among labeling dyes, wherein the contents of processing and the processed analytical data are obtained by the waveform processing means, and wherein the base sequence determining means outputs determined base sequence with a calculated degree of reliability for each base of the determined base sequence.

* * * * *